United States Patent [19]

Ryer et al.

[11] 4,049,564

[45] Sept. 20, 1977

[54] OXAZOLINE DERIVATIVES AS ADDITIVES USEFUL IN OLEAGINOUS COMPOSITIONS

[75] Inventors: Jack Ryer, East Brunswick; James Zielinski, Somerset; Harold N. Miller, Millington, all of N.J.; Stanley J. Brois, Wantage, England

[73] Assignee: Exxon Research & Engineering Co., Linden, N.J.

[21] Appl. No.: 543,240

[22] Filed: Jan. 23, 1975

Related U.S. Application Data

[63] Continuation-in-part of Ser. No. 455,250, March 27, 1974, abandoned, and a continuation-in-part of Ser. No. 530,235, Dec. 6, 1974, abandoned.

[51] Int. Cl.$^2$ .............................................. C10M 1/32
[52] U.S. Cl. ................................... 252/51.5 A; 44/63; 44/71; 44/72; 44/75; 252/51.5 R
[58] Field of Search ..................... 252/51.5 R, 51.5 A; 44/63, 71, 72, 75

[56] References Cited

U.S. PATENT DOCUMENTS

| 2,636,038 | 4/1953 | Brandner .................... 252/51.5 R X |
| 2,897,182 | 7/1959 | de Benneville et al. ... 252/51.5 R X |
| 3,184,474 | 5/1965 | Catto et al. ................. 252/51.5 A X |
| 3,329,658 | 7/1967 | Fields .......................... 252/51.5 A X |
| 3,516,944 | 6/1970 | Litt et al. .................... 252/51.5 R X |
| 3,966,620 | 6/1976 | Bridger et al. ............. 252/51.5 A X |

*Primary Examiner*—Delbert E. Gantz
*Assistant Examiner*—Andrew H. Metz
*Attorney, Agent, or Firm*—Roland A. Dexter

[57] ABSTRACT

Derivatives of Oxazoline reaction products of hydrocarbon substituted dicarboxylic acid, ester, or anhydride, for example octadecenylsuccinic anhydride and polyisobutenylsuccinic anhydride with 2,2-disubstituted-2-amino-1-alkanols, such as tris-hydroxymethylaminomethane (THAM) are useful additives in oleaginous compositions, such as sludge dispersants for lubricating oil, or anti-rust agents for gasoline.

10 Claims, No Drawings

OXAZOLINE DERIVATIVES AS ADDITIVES USEFUL IN OLEAGINOUS COMPOSITIONS

CROSS-REFERENCE TO RELATED CASES

This is a continuation-in-part of U.S. Pat. applications Ser. No. 455,250 filed Mar. 27, 1974 and Ser. No. 530,235 filed Dec. 6, 1974 and both now abandoned.

BACKGROUND OF THE INVENTION AND PRIOR ART

During the past decade, ashless sludge dispersants have become increasingly important, primarily in improving the performance of lubricants and gasoline in keeping the engine clean of deposits, and permitting extended crankcase oil drain periods. Most commercial ashless dispersants fall into several general categories. In one category, an amine or polyamine is attached to a long chain hydrocarbon polymer, usually polyisobutylene, obtained by the reaction of halogenated olefin polymer with polyamine as in U.S. Pat. Nos. 3,275,554; 3,565,592; 3,565,804. In another category, a polyamine is linked to the polyisobutylene through an acid group, such as long chain monocarboxylic acid, e.g., see U.S. Pat. No. 3,444,170 or long chain dicarboxylic acid such as polyisobutenylsuccinic anhydride, by forming amide or imide linkages, such as described in U.S. Pat. Nos. 3,172,892; 3,219,666; etc. More recently, non-nitrogen ashless dispersants have been formed by esterifying long chain dicarboxylic acids; such as the polyisobutenylsuccinic anhydride, with polyols, such as pentaerythritol, as in U.S. Pat. No. 3,381,022.

Reaction products of hydrocarbon substituted succinic anhydride, e.g., the aforesaid polyisobutenylsuccinic anhydride, with compounds containing both an amine group and a hydroxy group have been suggested or investigated in the prior art. For example, U.S. Pat. No. 3,272,746 teaches the reaction of ethanolamine and diethanolamine, as well as various hydroxyalkyl substituted alkylene amines, such as N-(2-hydroxyethyl) ethylene diamine, N,N'-bis(2-hydroxyethyl) ethylene diamine, with alkenyl succinic anhydride to obtain ashless dispersants for lube oil. A hydroxy amine, such as diethanolamine, is reacted with a long chain alkenylsuccinic anhydride in U.S. Pat. No. 3,324,033 to form a mixture of esters and amides, wherein some of the diethanolamine reacts through a hydroxy group to give an ester linkage, which another portion of the diethanolamine forms an amide linkage. U.S. Pat. No. 3,364,001 teaches a tertiary alkanolamine reacted with an alkenyl succinic anhydride to form an ester useful as a gasoline additive. U.S Pat. No. 3,448,049 teaches dispersants, corrosion inhibitors and antiwear agents in lubricants and fuels by esterifying alkenyl succinic anhydride with a hydroxy compound made by reacting an alkanolamine with an unsaturated ester, amide or nitrile. U.S. Pat. No. 3,630,904 teaches reacting a hydroxy amine, with both short and long chain dicarboxylic acid. U.S. Pat. No. 3,484,374 teaches the polymeric condensation products of polycarboxylic acid or anhydride with various alkanolamines such as aminoethylethanolamine. N-methyldiethanolamine, etc. United Kingdom patent specification No. 809,001 teaches corrosion inhibitors comprising a multiple salt complex derived from the reaction product of hydrocarbyl substituted dicarboxylic acids and hydroxy amines (including 2-amino-2-methyl-1,3-propanediol [AMP] and tris hydroxymethylaminomethane [THAM]) further complexed with mono- and polycarboxylic acids (see Examples 17-19).

U.S. Pat. No. 3,576,743 teaches reacting polyisobutenylsuccinic anhydride with a polyol, such as pentaerythritol, followed by reaction with THAM, (see Example 1). U.S. Pat. No. 3,632,511 teaches reacting polyisobutenylsuccinic anhydride with both a polyamine and a polyhydric alcohol including THAM. U.S. Pat. No. 3,697,428 (Example 11) teaches reacting polyisobutenylsuccinic anhydride with a mixture of pentaerythritol and THAM. United Kingdom patent specification 984,409 teaches ashless, amide/imide/ester type lubricant additives prepared by reacting an alkenyl succinic anhydride, said alkenyl group having 30 to 700 carbon atoms, with a hydroxy amine including THAM.

SUMMARY OF THE INVENTION

As noted above, the prior art teaches dispersants formed from hydrocarbyl substituted dicarboxylic acid material, usually alkenyl succinic anhydride, reacted with various amino or hydroxy compounds either through an amide, imide or ester linkage. In contrast to most of the prior art, the present invention is based upon the discovery that reaction of hydrocarbyl dicarboxylic acid material, i.e. acid or anhydride, or ester, with certain classes of amino alcohols, under certain conditions, will result in a heterocyclic ring structure namely an oxazoline ring, and that materials with this oxazoline ring including derivatives thereof can be tailored for various functions, such as anti-rust agents, detergents, or dispersants for oleaginous compositions including lube oil, gasoline, turbine oils and oils for drilling applications.

The derivative compounds of the invention have at least 8 carbons in the substantially saturated aliphatic hydrocarbyl group and at least one carboxylic acid group converted into an oxazoline ring as a result of the reaction of at least equimolar amounts of said hydrocarbon substituted $C_4$-$C_{10}$ mono-unsaturated dicarboxylic acid material and a 2,2-disubstituted-2-amino-1-alkanol having 2 to 3 hydroxy groups and containing a total of 4 to 8 carbons followed by reaction with a third reactant to form the derivative, said reactants including: amines; alkylene oxides; and glycols which react with said oxazoline-containing compound whereby the multifunctionality of the additive compound of the invention can be better tailored to its requisite use.

THE HYDROCARBYL DICARBOXYLIC ACID MATERIAL

The hydrocarbyl substituted dicarboxylic acid material, i.e., acid or anhydride, or ester, used in the invention includes alpha-beta unsaturated $C_4$ to $C_{10}$ dicarboxylic acid, or anhydrides or esters thereof, such as fumaric acid, itaconic acid, maleic acid, maleic anhydride, chloromaleic acid, dimethyl fumarate, etc., which are substituted with a hydrocarbon chain containing at least 8 carbons, preferably a long hydrocarbon chain of at least 50 carbons (branched or unbranched) e.g. an olefin polymer chain.

In general, these hydrocarbyl substituted dicarboxylic acid materials and their preparation are well known in the art as well as being commercially available, e.g., 2-octadecenylsuccinic anhydride and polyisobutylenesuccinic anhydride.

The hydrocarbyl portion optionally should average from at least about 16 carbon atoms per dicarboxylic acid group and be substantially saturated. Usually no more than 10 mole %, and preferably 5 mole % or less of the total carbon to carbon linkage will be unsaturated, as excessive unsaturation in the final product will tend to oxidize and unduly form gums and resins in the engine. Further descriptions and examples of the hydrocarbyl substituent portion are set forth in U.S. Pat. No. 3,272,746, column 2, line 35 to column 4, line 10, which is hereby incorporated in this application by reference. Further examples of the hydrocarbyl substituent portion are set forth in U.S. Pat. No. 3,458,444 which shows such dicarboxylic acids reacted with tertiary amines to produce rust and sludge inhibitors.

Frequently these hydrocarbyl substituted dicarboxylic acid materials are prepared by reacting the unsaturated dicarboxylic acid material, usually maleic anhydride, with a 1-olefin, e.g. an olefin polymer of at least about 30 carbons still retaining a terminal unsaturation. The olefin polymer can, if desired, be first halogenated, for example, chlorinated or brominated to about 2 to 5 wt. % chlorine, or about 4 to 8 wt. % bromine, based on the weight of polymer, and then reacted with the maleic anhydride (see U.S. Pat. No. 3,444,170).

In some cases, the olefin polymer may be completely saturated, for example an ethylene-propylene copolymer made by a Ziegler-Natta synthesis using hydrogen as a moderator to control molecular weight. In the case of such saturated polymers, then the polymer can be halogenated to make it reactive so it can be condensed with the unsaturated dicarboxylic acid material which is then randomly added along the polymer chain.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor molar amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have number average molecular weights within the range of about 750 and about 200,000, more usually between about 1000 and about 20,000. Particularly useful olefin polymers have number average molecular weights within the range of about 900 and about 3000 with approximately one terminal double bond per polymer chain. An especially valuable starting material for a highly potent dispersant additive made in accordance with this invention is polyisobutylene.

Especially useful when it is desired that the dispersant additives also possess viscosity index improving properties are 10,000 to 200,000, e.g., 25,000 to 100,000 number average molecular weight polymers. An especially preferred example of such a V.I. improving polymer is a copolymer of about 30 to 85 mole % ethylene, about 15 to 70 mole % $C_3$ to $C_5$ mono-alpha-olefin, preferably propylene, and 0 to 20 mole % of a $C_4$ to $C_{14}$ non-conjugated diene.

These ethylene-propylene V.I. improving copolymers or terpolymers are usually prepared by Ziegler-Natta synthesis methods, e.g., see U.S. Pat. No. 3,551,336. Some of these copolymers and terpolymers are commercially available, such as VISTALON®, an elastomeric terpolymer of ethylene, propylene and 5-ethylidene norbornene, marketed by Exxon Chemical Co., New York, N.Y. and NORDEL®, a terpolymer of ethylene, propylene and 1,4-hexadiene marketed by E. I. duPont de Nemours & Co.

Other halogenation techniques for attaching the dicarboxylic acid material to a long hydrocarbon chain, involve first halogenating the unsaturated dicarboxylic acid material and then reacting with the olefin polymer, or by blowing halogen gas, e.g., chlorine, through a mixture of the polyolefin and unsaturated dicarboxylic acid material, then heating to 150° to 220° C. in order to remove HCl gas, e.g., see U.S. Pat. Nos. 3,381,022 and 3,565,804.

THE AMINO ALCOHOL

The amino alcohol used to make the oxazoline dispersant is a 2,2-disubstituted-2-amino-1-alkanol, having 2 to 3 hydroxy groups, containing a total of 4 to 8 carbon atoms, and which can be represented by the formula:

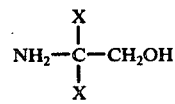

wherein X is an alkyl, or hydroxy alkyl group, with at least one of the X substitutents, and preferably both of the X substituents, being a hydroxy alkyl group of the structure $-(CH_2)_nOH$, wherein $n$ is 1 to 3.

Examples of such 2,2-disubstituted amino alkanols, include 2-amino-2-methyl-1,3-propanediol, 2-amino-2-(hydroxymethyl)-1,3-propanediol (also known as tris-hydroxyaminomethane or THAM), 2-amino-2-ethyl-1,3-propanediol, etc. Because of its effectiveness, availability, and cost, the THAM is particularly preferred.

THE OXAZOLINE REACTION CONDITIONS

The formation of the novel oxazoline materials, in a fairly higher yield, can be effected by adding about 1 to 2 mole equivalent of the aforesaid 2,2-disubstituted-2-amino-1-alkanol per mole equivalent of the dicarboxylic acid material, with or without an inert diluent, and heating the mixture at 140°–240° C., preferably 170°–220° C. for $\frac{1}{2}$ to 24, more usually 2 to 8 hours, followed by derivatization.

Although not necessary, the presence of small amounts, such as 0.01 to 2 wt. %, preferably 0.1 to 1 wt. %, based on the weight of the reactants, of a metal salt can be used in the reaction mixture as catalyst to shorten the reaction times. The metal catalyst can later be removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product, and depending on the metal, it may even contribute performance benefits to the oil or gasoline. This is believed to occur with the use of zinc catalysts in lubricants.

Inert solvents which may be used in the above reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc.

Metal salts that may be used as catalysts in the invention include carboxylic acid salts of Zn, Co, Mn and Fe. Metal catalysts derived from strong acids (HCl, sulfonic acid, $H_2SO_4$, $HNO_3$, etc.) and bases, tend to diminish the yield of the oxazoline products and instead favor imide or ester formation. For this reason, these strong acid catalysts or basic catalysts are not preferred and usually will be avoided. The carboxylic acids used to prepare the desired catalysts, include $C_1$ to $C_{18}$, e.g., $C_1$ to $C_8$, acids, such as the saturated or unsaturated mono and dicarboxylic aliphatic hydrocarbon acids, particularly fatty acids. Specific examples of such desired carboxylic acid salts include zinc acetate, zinc formate, zinc propionate, zinc stearate, manganese (ous) acetate, iron tartrate, cobalt (ous) acetate, etc. Completion of the oxazoline reaction can be readily ascertained by using periodic infrared spectral analysis for following the oxazoline formation (oxazoline peak forms at 6.0 microns), or by the cessation of water evolution.

REACTION MECHANISM OF THE OXAZOLINE FORMATION

While not known with complete certainty, but based on experimental evidence, it is believed that the reaction of the hydrocarbyl substituted dicarboxylic acid material, e.g., a substituted succinic anhydride, with the amino alcohol of the invention, e.g., two equivalents of 2,2-disubstituted-2-aminoethanol such as tris-hydroxymethylaminomethane (THAM), gives oxazoline, e.g., bis-oxazolines, via the intermediacy of several discrete reaction species. If an acid anhydride is used, the initial transformation appears to involve the scission of the anhydride by the amino function of one mole of the amino alcohol to yield an amic acid. Addition of another mole equivalent of amino alcohol is believed to form the amic acid amine salt, which then upon further heating, undergoes cyclo-dehydration to the final bis-oxazoline product. The catalyst effect of metal salts, such as zinc acetate ($ZnAc_2$), on oxazoline formation is very likely ascribable to the favorable polarization of the amide group by the zinc ion towards attack by the hydroxy function of the amino alcohol reactant. These reactions can be typified as follows in the case of bis-oxazoline:

thylaminomethane (THAM) represent a $-CH_2OH$ group.

In contrast to the above oxazoline formation using the disubstituted amino alcohol, if the amino alcohol has no substituents as in 2-aminoethanol, or has only one substituent in the 1- or 2-position as in 2-amino-1-propanol, 2-amino-1-butanol, and related mono-substituted 2-aminoethanols, the amino alcohol fails to undergo the aforesaid oxazoline forming reaction. Instead, these other amino alcohols will react with the succinic anhydride to give almost exclusively succinimide products as illustrated in the following reaction:

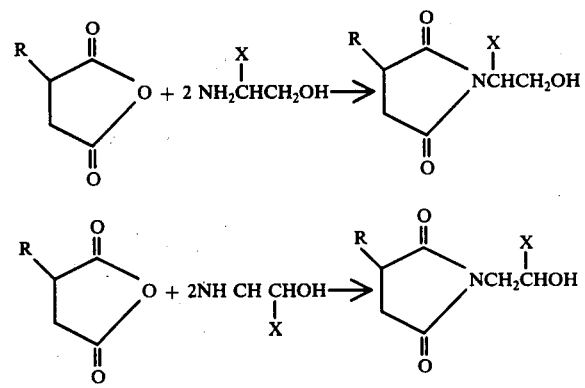

wherein R and X are as previously defined. In experiments on the above reactions, in no instance were discernible amounts of bis-oxazoline products found.

Condensation of about 1 mole equivalent of the disubstituted alkanol per mole equivalent of said dicarboxylic acid material affords the mono-oxazoline ester.

The reaction products of said alkanol and said dicarboxylic acids, wherein the molar equivalent of the former in the reaction ranges from at least one to about two, preferably about one, per mole equivalent of the latter results in products which can be usefully reacted with reactants including amines, alkylene oxides and polyols to produce the derivatives of the invention.

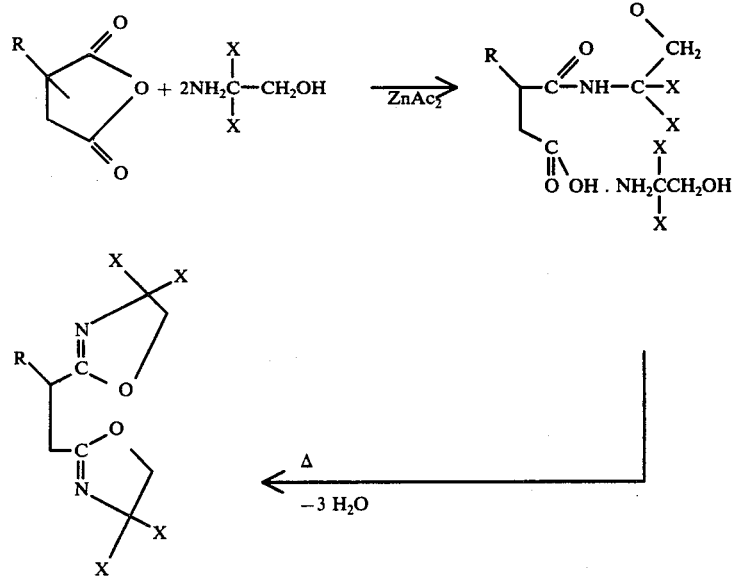

where R is the hydrocarbyl group of the succinic anhydride, and each X in this case of using tris-hydroxyme-

AMINES

Useful amine compounds for derivatization of the oxazoline additives according to this invention include amines of about 2 to 60, e.g. 3 to 20, total carbon atoms and about 1 to 12, e.g., 1 to 6 nitrogen atoms in the molecule, which amines may be hydrazines, or may include other groups, e.g., 1 to 4 hydroxyl groups, alkoxy groups, amido groups, imidazoline groups and the like.

Preferred amines are aliphatic, saturated amines, and include those of the general formulae:

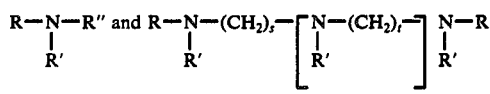

wherein R, R' and R" are independently selected from the group consisting of hydrogen; $C_1$ to $C_{12}$ straight or branched chain alkyl radicals; $C_1$ to $C_{12}$ alkoxy substituted $C_2$ to $C_6$ alkylene radicals; $C_2$ to $C_{12}$ hydroxy or amino alkylene radicals; and $C_1$ to $C_{12}$ alkylamino substituted $C_2$ to $C_6$ alkylene radicals; $s$ is 2 to 6, preferably 2 to 4; and $t$ is 0 to 10, preferably 2 to 6.

Examples of suitable amine compounds represented by the above include: n-octyl amine; n-dodecyl amine; di-(2-ethylhexyl) amine; 1,3-diaminoethane; 1,3-diaminopropane; 1,4-diaminobutane; 1,6-diaminohexane; diethylene triamine; triethylene tetramine; tetraethylene penta-amine; 1,2-propylene diamine; di-(1,2-propylene) triamine; di-(1,3-propylene) triamine; N,N-dimethyl-1,3-diaminopropane; N,N-di(2-aminoethyl) ethylene diamine; N,N-di-(2-hydroxyethyl)-1,3-propylene diamine; 3-dodecyl oxy propylamine; N-dodecyl-1,3-propane diamine; diethanol amine; morpholine; tris-hydroxymethylaminomethane (THAM); diisopropanol amine; etc.

Still other useful amine compounds include: alicyclic diamines such as 1,4-di(aminomethyl) cyclohexane and heterocyclic nitrogen compounds such as imidazolines and N-aminoalkyl piperazines of the general formula:

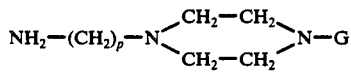

wherein G is independently selected from the group consisting of hydrogen and Ω-aminoalkylene radicals of from 1 to 3 carbon atoms; and $p$ is an integer of from 1 to 4. Non-limiting examples include 2-pentadecylimidazoline; N-(2-aminoethyl) piperazine; N-(3-aminopropyl) piperazine; and N,N'-di(2-aminoethyl) piperazine.

Other alkylene amino compounds that can be used include dialkylaminoalkyl amine such as dimethylaminoethylamine, dimethylaminoproylamine, methylpriopylaminoamylamine, etc. These may be characterized by the formula:

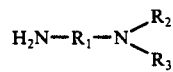

wherein $R_1$ is an alkylene radical, e.g., an ethylene, propylene, or butylene radical, and $R_2$ and $R_3$ are $C_1$ to $C_5$ alkyl radicals.

Commercial mixtures of amine compounds may advantageously be used for the preparation of the polyamino compositions of this invention. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylene tetramine, tetraethylene penta-amine and isomeric piperazines. Low cost poly(ethylene amines) compounds having a composition approximating tetraethylene pentamine are available commercially under the trade names Polyamine H and Polyamine 400 (PA-400). A similar mixture sold as Polyamine 500 (PA-500) is marketed by Jefferson Chemical Co., New York, N.Y. Similar materials may be made by the polymerization of aziridine, 2-methylaziridine and azetidine.

The more important alkylene polyamine or aliphatic polyamine compound, used in this invention, can be broadly characterized as an alkylene amino compound containing from 2 to 12 nitrogen atoms where pairs of nitrogen atoms are joined by alkylene groups of from 2 to 4 carbon atoms.

Reaction of the amine compound with the oxazoline additive readily takes place in an inert solvent containing both compounds at a temperature in the range of about 400° to 300° C, preferably at a temperature in the range of 100° to 200° C. Useful amine salts can be prepared by mixing the reactants at room temperature.

ALKYLENE OXIDES

Oxazoline products, with remaining carboxylic acid groups, can be further reacted with 1 to 30, e.g. 1 to 10, moles of a $C_2$ to $C_3$ alkylene oxide, i.e. ethylene oxide or propylene oxide.

Generally, the reaction is carried out by adding the alkylene oxide portionwise to the oxazoline additive at somewhat elevated temperatures. Temperatures within the range of 50° to 100° C., for example, are generally satisfactory and the alkylene oxide may be added conveniently beneath the surface of a solution of oxazoline in inert solvent. The alkylene oxide reacts immediately as it is added, and when it has all been added, the reaction is essentially complete. It is believed that the alkylene oxides, particularly, can be usefully reacted with the bis-oxazoline product.

USE OF THE OXAZOLINE ADDITIVE IN OLEAGINOUS COMPOSITIONS

The oil soluble oxazoline reaction products of this invention can be incorporated in a wide variety of oleaginous compositions. They can be used in lubricating oil compositions, such as automotive crankcase lubricating oils, automatic transmission fluids, etc. in concentrations generally within the range of about 0.10 to 20 weight percent, e.g., 0.1 to 10 weight percent, preferably 0.3 to 3.0 weight percent, of the total composition. The lubricants to which the oxazoline products can be added include not only hydrocarbon oils derived from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multifunctional additives having detergents, anti-rust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oil streams in refinery operations to prevent fouling of process equipment such as heat exchangers or in turbine oils, about 0.001 to 2 wt. % will generally be used.

The additive may be conveniently dispensed as a concentrate comprising a minor proportion of the additive, e.g., 2 to 45 parts by weight, dissolved in a major proportion of a mineral lubricating oil, e.g., 98 to 45 parts by weight, with or without other additives being present.

In the above compositions or concentrates, other conventional additives may also be present including dyes, pour point depressants, antiwear agents such as tricresyl phosphate or zinc dialkyldithiophosphates of 3 to 8 carbon atoms in each alkyl group, antioxidants, such as N-phenyl α-naphthylamine, tert-octylphenol sulfide, 4,4'-methylene bis(2,6-ditert-butyl phenol), viscosity index improvers such as ethylene-propylene copolymers, polymethacrylates, polyisobutylene, alkyl fumarate-vinyl acetate copolymers and the like, deemulsifiers such as polysiloxanes, ethoxylated polymers and the like.

This invention will be further understood by reference to the following examples, which include preferred embodiments of the invention.

EXAMPLE 1

A mono-oxazoline of octadecenylsuccinic anhydride and tris-hydroxymethylaminomethane (THAM) was prepared as follows:

A mixture of 87.8 gm. (0.24 moles) of 2-octadecenyl-succinic anhydride, commercially available from Humphrey Chemical or Monsanto, St. Louis, Missouri, 0.5 gm. of zinc acetate dihydrate ($ZnAc_2.2H_2O$) as a catalyst and 30.75 gm. (0.25 mole) of tris-hydroxymethylaminomethane (THAM) was charged into a laboratory glass 1 liter reaction flask, equipped with a bottom draw-off, a thermometer, a charging funnel, a nitrogen bleed, and an overhead condenser equipped with a Deane-Starke water trap. The flask was heated in an oil bath. When the reaction temperature had risen to 210° C. the reaction was continued at this temperature until the evolution of water ceased. A sample of the product was recrystallized from acetone/hexane solution and submitted to elemental analysis which showed 71.00 wt. % carbon (calculated 71.68 wt. %); 10.33 wt. % hydrogen (calculated 10.41 wt. %); and 4.12 wt. % nitrogen (calculated 3.22 wt. %). The calculation was based on $C_{26}H_{45}NO_4$. The infrared spectrum of the product featured strong ester and oxazoline absorption and at 5.75 and 6.0 microns, respectively. The molecular weight of the product by osmometry was found to be 2324 (vapor phase osmometry).

EXAMPLE 2

Approximately 0.2 mole of polyisobutenylsuccinic anhydride (Sap. No. 80) was charged into a reactor and heated to 205° C. under a nitrogen blanket. To the stirred reactant were added 0.2 mole (24.2 g.) of tris-hydroxymethylaminomethane, in portions over an hour period. Thereafter, the mixture was stirred at 205° C. for about 3 hours while water distilled from the reactor. Upon cooling, half of the reaction mixture was dissolved in an equal weight percent of Solvent 150 Neutral oil. The resulting oil solution as then diluted with 500 ml. of hexane and the resulting hexane solution was washed three times, each with a 250 ml. portion of methanol. Rotoevaporation of the hexane layer afforded a concentrate which analyzed for 0.50 wt. % nitrogen and 2.37 wt. % oxygen, and featured a TAN (total acid numer) of 0.16. The experimentally found O/N ratio of 4.7 was in excellent agreement with the theoretical O/N ratio of 4.6. Furthermore, a strong absorption band at 6.0 microns in infrared spectrum of the product indicated a mono-oxazoline structure formed. Another strong absorption band at 5.75 micron indicated an ester structure had also formed, which is believed to be between one of the hydroxy groups extending from an oxazoline ring with a carboxy group of the polyisobutenylsuccinic anhydride.

EXAMPLE 3

1335 grams of polyisobutenylsuccinic anhydride having a Sap. No. of about 80 was charged into a 1 liter 4-necked flask, and heated to 205° C. The reactant was stirred under a nitrogen sparge and blanket and 121 grams of trishydroxymethylaminomethane were added over a 1 hour period, being careful to avoid foaming. The course of reaction was monitored by infrared spectroscopy, which indicated that the reaction was essentially complete after eight hours. The neat product analyzed for 1.12 wt. % nitrogen and featured a number average molecular weight of 3034 (by vapor pressure osmometry). The infrared spectrum of the product showed the expected ester and oxazoline bands at 5.75 and 6.02 microns, respectively.

EXAMPLE 4

53.4 pounds of polyisobutenylsuccinic anhydride (PIBSA) with a Sap. No. of about 80 was charged into a reactor and heated to 435° F. The PIBSA reactant was stirred and sparged with nitrogen, and 4.84 pounds of tris-hydroxymethylaminomethane were added over an hour period. Reaction was continued until water evolution has ceased. The product was diluted with an equal weight of Solvent 150 Neutral Oil and showed ester and oxazoline absorptions in the infrared. The oil solution analyzed for 0.51 wt.% nitrogen and by infrared measurement indicated that about 99% of the THAM had been converted into the oxazoline structure. Similarly the products of Examples 1, 2 and 3 upon infrared measurement indicated that about 100%, 95% and 98% of the THAM, respectively, had been converted into the oxazoline structure.

In Examples 2–4 the PIBSA had been prepared by conventional techniques, namely the reaction of clorinated polyisobutylene having a chlorine content of about 3.8 wt. %, based on the weight of chlorinated polyisobutylene, and an average of 70 carbon atoms in the polysiobutylene group, with maleic anhydride at about 200° C. The resulting polyisobutylenesuccinic anhydride showed a saponification number of 80 mg KOH/gm. The molecular weight of the polyisobutylene group of said PIBSA was 980 as measured by vapor phase osmometry.

EXAMPLE 5

Approximately 0.05 moles (71 grams) of the monooxazoline reaction product of polyisobutenylsuccinic anhydride (0.2 mole) and tris-hydroxymethylaminomethane (0.2 mole) was dissolved in 50 ml. of xylene using a 500 ml. 4-necked flask. To this solution as added 0.05 moles (9.5 grams) of tetraethylene pentamine (a commercially available polyamine containing 32.38 wt. % of nitrogen) designated as Polyamine E-100 and sold by Dow Chemical. Reflux was carried out at 145° C. for 3 hours utilizing a Dean Starke trap. The xylene was removed after which the product was heated to 190° C. for 1.5 hours and thereafter recovered.

EXAMPLE 6

The process of Example 5 was carried out except that the 0.05 moles of tetraethylene pentamine was replaced by 0.05 moles of diethylene triamine.

EXAMPLE 7

The process of Example 5 was carried out except that the 0.05 moles of tetraethylene pentamine was replaced by 0.05 moles of diethylene glycol.

Infrared analysis of the products of Examples 5 and 6 showed the presence of the oxazoline ring at substantially the same level and disappearance of the ester linkage extant in said mono-oxazoline reaction products.

The products of Examples 5, 6 and 7 were tested for their effectiveness as gasoline anti-rust agents. Each product was first dissolved in xylene, and the solution was added to the gasoline to incorporate the additive at a treat rate of 12 pounds of oxazoline additive per thousand barrels of gasoline. The gasoline so treated was then tested for rust according to ASTM-D-665M rust test. In brief, this test is carried out by observing the amount of rust that forms on a steel spindle after rotating for an hour in a water-gasoline mixture. In each case, the oxazoline treated gasoline gave no rust indicating that each product was very effective as an anti-rust additive since the untreated gasoline will give rust over the entire surface of the spindle.

The oxazoline reaction products of the invention which are primarily useful and an anti-rust additive and/or detergent for gasoline will generally have hydrocarbyl substitutents nunbering from about 12 to about 49 carbons (preferred is about 8 as exemplified by 2-octadecenyl); whereas, for applications as a dispersant or detergent in lubricants it is preferred that the hydrocarbyl substituents number from at least about 30 carbons, e.g., at least 45 carbons.

The chemical structure, number of the oxazoline rings and character of the derivative have an influence on the functionality of the additive compounds of the invention.

In summary, effective additives for oleaginous compositions can be prepared by reaction of a hydrocarbon substituted dicarboxylic acid material with a 2,2-disubstituted-2-amino-1-alkanol under conditions such that formation of simple esters, imides or amides is eliminated, or at least minimized, so that a substantial proportion of the amino alkanol is converted into oxazoline rings. Infrared spectrum on some of the aforesaid Examples indicate that a major proportion, i.e. from about 90% to about all of the amino-alkanol was converted to oxazoline rings.

As evidenced by the Example 7, it is seen that ester derivatives of the oxazoline reaction products can be produced. In addition to the diethylene glycol of Example 7 other polyols such as pentaerythritol, trimethylol propane, ethylene glycol, propylene glycol, cellosolve, carbitol, etc. can be used to prepare the ester derivatives.

The invention in its broader aspect is not limited to the specific details shown and described and departures may be made from such details without departing from the principles of the invention and without sacrificing its chief advantages.

What is claimed is:

1. A composition comprising a major amount of a liquid hydrocarbon of the class consisting essentially of fuels and lubricating oils and a minor but dispersing amount of a liquid hydrocarbon soluble derivative of the oxazoline reaction product of a substantially saturated aliphatic hydrocarbyl substituted $C_4$–$C_{10}$ mono-unsaturated dicarboxylic acid material selected from the group consisting of acids, acid anhydrides and esters having at least about 8 carbon atoms in said hydrocarbyl group with from at least 1 to about 2 mole equivalent, per moel equivalent of said dicarboxylic acid material, of a 2,2-disubstituted-2-amino-1-alkanol having 2 to 3 hydroxy groups and containing a total of 4 to 8 carbons, and which is represented by the formula:

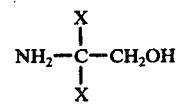

wherein X is an alkyl or hydroxyl alkyl group, with at least one of the X substituents being a hydroxyl alkyl group of the structure —$(CH_2)_n$OH wherein $n$ is 1 to 3, said reaction conditions being at a temperature of from about 140° to 240° C. for from ½ to 24 hours whereby at least one carboxylic acyl group is converted into an oxazoline ring, said reaction product being derivatized by reaction with a member of the group consisting of:
 a. an aliphatic, saturated amine containing 2 to 60 carbon atoms and 1 to 12 nitrogen atoms and of the general formulae:

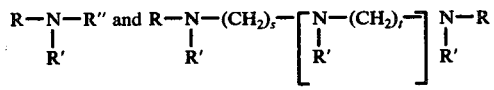

wherein R, R' and R" are independently selected from the group consisting of hydrogen; $C_1$ to $C_{12}$ straight or branched chain alkyl radicals; $C_1$ to $C_{12}$ alkoxy substituted $C_2$ to $C_6$ alkylene radicals; $C_2$ to $C_{12}$ hydroxy or amino alkylene radicals; and $C_1$ to $C_{12}$ alkylamino substituted $C_2$ to $C_6$ alkylene radicals; $s$ is 2 to 6 and, $t$ is 0 to 10; and,
 b. a polyol selected from the group consisting of diethylene glycol, pentaerythritol, trimethylol propane, ethylene glycol, propylene glycol, glycol ethyl ether and diethylene glycol ethyl ether.

2. A composition according to claim 1, wherein said oxazoline reaction product is the mono-oxazoline product of an alkenyl succinic anhydride or acid which has been reacted with about one mole equivalent of trishydroxy methyl aminomethane, said alkenyl substituent having a number average molecular weight within the range of about 1000 and about 20,000.

3. A composition according to claim 1 wherein said oxazoline reaction product is the mono-oxazoline product of hydrocarbon substituted succinic anhydride reacted with about one mole equivalent of tris-hydroxymethylaminomethane, said mono-oxazoline being further derivatized by reaction with about a molar proportion of an alkylene polyamine containing 2 to 12 nitrogen atoms, and wherein pairs of nitrogen atoms are joined by alkylene groups of 2 to 4 carbon atoms.

4. A composition according to claim 1, wherein said oil material is gasoline, said hydrocarbon contains about 12 to 49 carbon atoms and said polyol is diethylene glycol.

5. A composition according to claim 4, wherein said hydrocarbon substituted succinic anhydride is octadecenyl succinic anhydride.

6. An oleaginous composition according to claim 1, wherein said oily material is a mineral lubricating oil, and the amount of said reaction product is in the range of about 0.01 to 10 wt. %, based on the total weight of said composition.

7. An oleaginous composition according to claim 1, wherein said material is a hydrocarbon fuel containing about 0.001 to 0.5 wt. %, based on the weight of the total composition, of said reaction product.

8. A composition according to claim 7, wherein said fuel is gasoline.

9. A compositioncomprising a major amount of a liquid hydrocarbon of the class consisting essentially of fuels and lubricating oils and a minor but dispersing amount of a liquid hydrocarbon soluble derivative of the oxazoline reaction product of a polyisobutylene substituted $C_4$-$C_{10}$ mono-unsaturated dicarboxylic acid material selected from the group consisting of acids, acid anhydrides and esters with from at least 1 to about 2 mole equivalent, per mole equivalent of said dicarboxylic acid material, of a 2,2-disubstituted-2-amino-1-alkanol having 2 to 3 hydroxy groups and containing a total of 4 to 8 carbons, and which is represented by the formula:

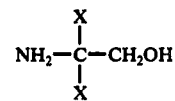

wherein X is an alkyl or hydroxyl alkyl group, with at least one of the X substituents being a hydroxyl alkyl group of the structure —$(CH_2)_n$OH wherein $n$ is 1 to 3, said reaction conditions being at a temperature of from about 140° C to 240° C. for from ½ to 24 hours whereby at least one carboxylic acyl group is converted into an oxazoline ring, said reaction product being derivatized by reaction with an alkylene polyamine containing 2 to 12 nitrogen atoms and wherein pairs of nitrogen atoms are joined by alkylene groups of 2 to 4 carbon atoms, said polyisobutylene substituent having a molecular weight of from 900 to 3000.

10. A composition according to claim 9, wherein said amine is tetraethylene pentamine.

* * * * *